United States Patent [19]

Horst

[11] Patent Number: 5,200,428
[45] Date of Patent: Apr. 6, 1993

[54] AGENT FOR THE TSH SUPPRESSION AND TREATMENT OF STRUMA

[75] Inventor: Claus Horst, Berlin, Fed. Rep. of Germany

[73] Assignee: Henning Berlin GmbH, Berlin, Fed. Rep. of Germany

[21] Appl. No.: 748,882

[22] Filed: Aug. 23, 1991

[30] Foreign Application Priority Data

Aug. 23, 1990 [DE] Fed. Rep. of Germany ....... 4026600

[51] Int. Cl.$^5$ ........................................... A61K 31/195
[52] U.S. Cl. ................................................... 514/561
[58] Field of Search ......................................... 514/561

[56] References Cited

PUBLICATIONS

Chem. Abst. 89-140 822 G.
Merck Index, p. 423 9th Ed (1976).
G. Hintze et al., "Controlled Study on the Therapeutic Effect of Iodine and Thyroxine in Patients with Simple Goitre," ACTA ENDOCRINOL., Band 102, Suppl. 253, p. 130 (1983).
N. R. Stasilli et al., "Antigoitrogenic and Calorigenic Activities of Thyroxine Analogues in Rats," Endocrinology, Band 64, No. 1, pp. 62-82 (1959).
E. C. Jorgensen et al., "Thyroid Hormone Analogs: Correlations Between Structure, Nuclear Binding and Hormonal Activity," Int. Congr. Ser.-Excerpta Med., Band 403; Endocrinology, Band 2, pp. 117-120 (1977).
C. Horst e al., "Rapid Stimulation of Hepatic Oxygen Consumption by 3,5-di-iodo-L-thyronine," Biochem. J., vol. 261, No. 3, pp. 945-950 (1989).

Primary Examiner—S. J. Friedman
Attorney, Agent, or Firm—Wegner, Cantor, Mueller & Player

[57] ABSTRACT

The agent for TSH suppression and for treatment of struma contains a therapeutically effective dose of 3,5-diiodo-L-thyronine and conventional galenic auxiliary materials.

4 Claims, No Drawings

AGENT FOR THE TSH SUPPRESSION AND TREATMENT OF STRUMA

Detailed comparative investigations of the activities of thyroxine and thyroxine-analogues in rats have resulted in the finding that the 3,5,3'-triiodo-L-thyronine (T3) having one iodine atom less than thyroxine has a higher activity than thyroxine itself. All of the other derivatives were clearly less active; cf. Neil R. Stasilli, Endocr. 64, pages 62 to 82 (1959). More particularly, upon comparison of the activities it had been established that any 3-mono-iodo and 3,5-diiodo compound that had not been iodo-substituted also in the 3'- and/or 5'-positions was inactive, with one exception being 3,5-diiodo-L-thyronine (T2), which still exhibits some weak activity; cf. Table 1, No. 38, page 68, paragraph 2, and page 80, paragraph 2. These results have been later on confirmed several times; cf. Eugene C. Jorgensen, in "Hormonal Proteins and Peptides" (ed: Li CH), Volume 6, Acad. Press New York 1978, in Table III on pages 132 and 133. Recent comparative investigations of thyroxine, triiodo-thyronine and 3,5- diiodothyronine with respect to the oxygen consumption of the liver of hypothyroid rats have shown that 3,5-diiodo-L-thyronine stimulates slightly faster and that 3,5-diiodo-L-thyronine is the active principle with respect thereto; cf. Claus Horst et al., Biochem. J. (1989) 261, pages 945 to 950. Thus, 3,5-diiodo-L-thyronine is to be considered as a metabolite of the more highly iodinated and highly active substances, which metabolite has a direct influence on the mitochondria. Furthermore it should be noted that 3,5-diiodo-L-thyronine has a very fast onset, while T3 possesses a long-term effect.

In the course of intensive comparative studies of the effects of highly active derivatives of triiodo-thyronine on metabolic parameters such as free fatty acids, triglycerides and glucose, 3,5-diiodo-L-thyronine was included in the investigations, and it was confirmed that there is hardly any significant activity. However, it was unexpectedly determined that 3,5-diiodo-L-thyronine, in a long-term application taking weeks, in a highly significant manner reduces the TSH (thyroid stimulating hormone) level and, hence, is suitable as a highly efficient agent for the treatment of struma or goiter. This high activity of 3,5-diiodo-L-thyronine obviously has gone unnoticed in the past, because it exhibits this activity only when applied over an extended period of time. Thus the earlier experiments had obviously been scheduled over too short a term. Furthermore, what had been measured was not TSH, but the effects of the individual substances were evaluated on the regression of a previously induced struma. The fact has certainly contributed to such a misinterpretation that 3,5-diiodo-L-thyronine is also ineffective with respect to other parameters, namely with respect to the enzyme glycerol-1-phosphate dehydrogenase, the classic enzyme for the thyroid hormone activity, and to bonding to the cell nuclei; cf. Leeson et al., 1988, J. Med. Chem. 31, pages 37 to 54. Since 3,5-diiodo-L-thyronine in a low dosage virtually has no effect on metabolism, it is excellently suitable for TSH suppression and treatment of struma. Thus, the dosage may be selected on an order of magnitude comparable to that of thyroxine, however without exhibition of any of the side-effects caused by the latter.

Thus, the present invention, under a first aspect, relates to an agent for TSH suppression and for the treatment of struma in a mammal in need thereof, which agent contains a therapeutically effective dose of 3,5-diiodo-L-thyronine and conventional galenic auxiliary materials. The agent preferably contains from 1 to 5 mg of the active ingredient 3,5-diiodo-L-thyronine per dosage unit.

The present invention further relates to the method of use of 3,5-diiodo-L-thyronine in a mammal for the suppression of TSH and for the treatment of struma and to the use of 3,5-diiodo-L-thyronine for the preparation of an agent for TSH suppression and for the treatment of struma.

Furthermore, the present invention relates to a method for TSH suppression and for the treatment in a mammal of struma by the administration of therapeutically effective doses of 3,5-diiodo-L-thyronine.

As the forms for administration there may be considered in the first place tablets, dragées, but also drops and syrup. The active substance may also be administered in the form of soft gelatin capsules or hard gelatin capsules. Acceptable pharmaceutical carriers such as pregelatinated starch, corn starch, microcrystalline cellulose, highly dispersed silica or hydrogenated castor oil can be used. The tablets, dragées or capsules also may be coated to be resistent to gastric juice. It is important that in all cases a therapeutically effective dose is applied. Due to the long duration of activity, this dose may be administered daily in one portion. However, if so desired, it is also feasible that the conventional standard of three dosage units given per day is used. Thus, one dosage unit should contain from 1 to 5 mg of 3,5-diiodo- L-thyronine.

From the subsequent experimental results it will be evident to which degree 3,5-diiodo-L-thyronine causes a TSH suppression. For this determination, euthyroid rats, hypothyroid rats and adipose rats were treated with 3,5-diiodo-L-thyronine for 2 to 3 weeks, and the TSH levels were measured besides other parameters. The following results were obtained:

| Animals Tested | Dose Employed µg per 100 g of Body Weight | Level Observed of TSH ng per ml of Serum |
| --- | --- | --- |
| Euthyroid Rats (14 days) | | |
| Control (NaCl) | | 2.04 |
| Test Substance[1] | 10 | 1.42 |
| Test Substance | 100 | 0.88 |
| Hypothyroid Rats (14 days) | | |
| Control (NaCl) | | 25.70 |
| Test Substance | 100 | 3.20 |
| Adipose Rats (21 days) | | |
| Control (NaCl) | | 4.00 |
| Test Substance | 10 | 2.78 |
| Test Substance | 100 | 2.51 |

[1]Test substance 3,5-diiodo-L-thyronine.

For comparison, 15 µg of triiodo-thyronine (T3) were applied. Thereupon the TSH level decreased to 0.67 ng/ml in euthyroid rats and to 3.40 ng/ml in hypothyroid rats. The measurement of the thyroxine serum level resulted in a corresponding decrease.

Upon the administration of these doses, no change in the glucose level was found, while a shift of so far not significant extent was observed from triglycerides to free fatty acids.

I claim:

1. A method for suppression of TSH which comprises oral administration to a goiter patient in need thereof of a therapeutically effective dose 3,5-diiodo-L-thyronine.

2. The method of claim 1 wherein the dosage unit is 1-5 mg of 3,5-diiodo-L-thyronine.

3. A method of treatment of goiter wherein there is orally administered an effective amount of 3,5-diido-L-thyronine to a goiter patient in need thereof.

4. The method of claim 3 wherein the amount is 1-5 mg of 3,5-diiodo-L-thyronine.

* * * * *